United States Patent [19]

Brussee et al.

[11] Patent Number: 5,493,047

[45] Date of Patent: Feb. 20, 1996

[54] METHOD OF PREPARING OPTICALLY ACTIVE CYANOHYDRIN DERIVATIVES

[75] Inventors: Johannes Brussee; Arne Van Der Gen; Erwin G. J. C. Warmerdam; Chris G. Kruse, all of Weesp, Netherlands

[73] Assignee: Duphar International Research B.V., Weesp, Netherlands

[21] Appl. No.: 161,420

[22] Filed: Dec. 6, 1993

[30] Foreign Application Priority Data

Dec. 9, 1992 [EP] European Pat. Off. .............. 92203818

[51] Int. Cl.$^6$ ....................... C07C 253/30; C07C 253/32
[52] U.S. Cl. .................... 558/354; 558/398; 558/399; 558/406; 546/330; 548/531; 549/71; 549/484
[58] Field of Search ..................... 558/354, 398, 558/399; 546/330; 548/531; 549/71, 484

[56] References Cited

U.S. PATENT DOCUMENTS

| | | | |
|---|---|---|---|
| 4,997,970 | 3/1991 | Ager, Jr. ..................... | 558/354 |
| 5,110,976 | 5/1992 | Hidasi et al. .................. | 558/354 X |
| 5,128,497 | 7/1992 | Ager ........................... | 558/354 |
| 5,153,349 | 10/1992 | Zoltan et al. ................... | 558/354 |

FOREIGN PATENT DOCUMENTS

| | | | |
|---|---|---|---|
| 0601237 | 6/1994 | European Pat. Off. .............. | 558/354 |
| 2902466 | 8/1979 | Germany . | |
| 4103201 | 8/1992 | Germany . | |

OTHER PUBLICATIONS

*J. Am. Chem. Soc*, (1988) 110, pp. 6487–6491, D. L. Hughes et al., "A Mechanistic Study of the Mitsunobu Esterification Reaction".

*J. Org. Chem.*, (1989) 54, pp. 3045–3049, David Camp et al., "Mechanism of the Mitsunobu Esterification Reaction. 1. The Involvement of Phosphorances and Oxyphosphonium Salts".

*Angew. Chem.* 103 (1991) Nr. 7, 103, pp. 866–867, Von Franz Effenberger et al., "Darstellung und stereoselektive Reaktionene von (R)–α–Sulfonyloxnitrilen".

*J. Org. Chem.*, (1987), pp. 4978–4984, Teodozyj Kolasa et al., "Rections of α–Hydroxy Carbonyl Compounds with Azodicarboxylates and Triphenylphosphine: Synthesis of α–N–Hydroxy Amino Acid Derivatives".

*Synthesis*, (1981) pp. 1–28, Oyo Mitsunobu, "The Use of Diethyl Azodicarboxylate and Triphenylphosphine in Synthesis and Transformation of Natural Products".

*Tetrahedron Letters*, vol. 30, No. 23, (1989), pp. 3057–3058, H. Waldmann.

Camp, et. al.; J. Org. Chem. (1989), 54, pp. 3049–3054.

*Primary Examiner*—Joseph Paul Brust
*Attorney, Agent, or Firm*—Stevens, Davis, Miller & Mosher

[57] ABSTRACT

The invention relates to a method of preparing an optically active cyanohydrin carboxylic acid ester from an optically active cyanohydrin of opposite configuration, wherein said starting cyanohydrin is converted with a carboxylic acid in the presence of a dialkyl azodicarboxylate and a triarylphosphine.

The invention also relates to a method of preparing an optically active cyanohydrin of opposite configuration by a subsequent solvolysis of the ester obtained under conservation of the configuration.

4 Claims, No Drawings

METHOD OF PREPARING OPTICALLY ACTIVE CYANOHYDRIN DERIVATIVES

The present invention relates to a method of preparing an optically active cyanohydrin derivative from an optically active cyanohydrin of opposite configuration.

Cyanohydrins are versatile starting compounds or intermediates for the production of biologically active substances, which may be used e.g. in pharmaceutical compositions, for human or veterinary application, or in crop protection agents. Various of such active substances contain one or more chiral centres in their molecular structure, and therefore give rise to optical isomerism. It is generally known in the art, that often only one of the enantiomers presents the desired biological activity. The presence of the other optical antipods in a composition or agent may cause or invigorate certain side effects and burden the recipient, i.c. the human or animal body, or the environment, respectively. It is generally deemed more and more desirable to administer the biologically active substance in the form of a substantially single optical isomer, which specifically exhibits the desired biological activity, the so-called eutomer, and not in the form of a mixture of optical isomers, containing also the other, differently behaving antipode, the so-called distomer, in a substantial amount. Cyanohydrins may also be used for the production of other technically important materials for which high enantiomeric purities are required, such as liquid crystals.

In connection with the above there is an increasing number of publications in the field of producing optically active cyanohydrins, reflecting the growing demand for these compounds as starting compounds or synthetic building blocks for the production of biologically active substances. Since decades it is already known that the class of hydroxynitrile lyases catalyses the formation of specific optically active cyanohydrins by the stereoselective addition of hydrogen cyanide to the corresponding carbonyl compounds. Whereas, however, an optically active cyanohydrin possessing the specific configuration (generally the R-configuration) generated by using the readily available enzyme mandelonitrile lyase (R-oxynitrilase, E.C. 4.1.2.10) as a biocatalyst, is usually well accessible, synthesis of the cyanohydrin optical antipods (generally having the S-configuration) is hampered by the limited availability of the required biocatalysts, e.g. S-oxynitrilase from Sorghum, and their narrow substrate specificity. It is therefore of considerable interest to find a-method for the inversion of the configuration, more in particular for the chemical conversion of readily accessible cyanohydrins of specific configuration into their optical antipodes or derivatives thereof.

In connection herewith, Effenberger et al. have recently reported on their attempts to accomplish this inversion of configuration via a conversion into α-sulfonyloxynitriles: Angew. Chem., 1991, 103, 866–867; DE-A-4103201. By converting the hydroxy group present in optically active cyanohydrins into a better leaving group, viz. a sulfonyloxy group, Effenberger and coworkers have obtained satisfactory results. Inversion of the configuration was indeed observed, when optically active α-sulfonyloxynitriles, derived from saturated aliphatic aldehydes, were reacted with suitable nucleophiles. In this manner, (R)- 2-hydroxyvaleronitrile could be converted via the corresponding tosylate into (S)-2-acetoxy-valeronitrile, by using acetate anions as the nucleophile. The authors conclude from their results, that in this example the nucleophilic substitution occurs exclusively by a $S_N2$-mechanism. Effenberger et al., however, observed racemization instead of inversion of the configuration if aromatic cyanohydrins, in particular R-mandelonitrile, were used as substrates. So apparently in that case no cyanohydrin derivative of opposite configuration is obtained. Further it turned out, that the intermediate α-sulfonyloxynitriles are rather unstable, which hampers their purification and therefore impedes a practical realization of the intended conversion.

It is well documented, e.g. in a review by Mitsunobu in Synthesis, 1981, 1–28, that inversion of the configuration of certain hydroxy compounds, e.g. of sec. alcohols, can be achieved by an esterification reaction in the presence of diethyl azodicarboxylate and triphenylphosphine. The Mitsunobu reaction also occurs via a $S_N2$-reaction mechanism, extensively studied and described in literature (e.g. Hughes et al., J. Am. Chem. Soc., 1988, 110, 6487–6491; Camp et al., J. Org Chem., 1989, 54, 3045–3054). Therefore there exists a mechanistic relationship between the above-mentioned conversion described by Effenberger et al. and the Mitsunobu reaction. Up to the present, however, no attempt to use the Mitsunobu esterification for the inversion of the configuration of cyanohydrins has been reported. Kolasa et al. (J. Org. Chem., 1987, 52, 4978–4984) have treated rac. mandelonitrile under Mitsunobu conditions. They observed the formation of an ester (61), presumably formed by oxidation of some of the mandelonitrile. Apparently such oxidation reactions readily occur if α-hydroxycarbonyl compounds, having a relatively acidic α-proton, are treated under Mitsunobu conditions.

Notwithstanding the above-mentioned discouraging results, attempts have been made to convert optically active cyanohydrins derived from saturated aliphatic aldehydes, known as successful substrates in Effenberger et al.'s inversion reaction, to cyanohydrin carboxylic acid esters of opposite configuration. Surprisingly it appeared from these experiments, however, that not the expected cyanohydrin carboxylic acid esters of opposite configuration were obtained, but instead the cyanohydrin carboxylic acid esters of unchanged configuration. So the desired inversion of configuration clearly did not occur and the conclusion must be drawn, that the intended inversion of configuration by the above Mitsunobu esterification did not proceed.

Contrary to expectation, however, it has now been found, that inversion of the configuration of cyanohydrins under Mitsunobu esterification conditions can yet be achieved, if benzylic or allylic substrates, which are inappropriate in Effenberger et al.'s conversion, are applied.

So the present invention relates to a method of preparing an optically active cyanohydrin derivative from an optically active cyanohydrin of opposite configuration, which method is characterized in that an optically active cyanohydrin of the general formula

having either the R or the S configuration, and wherein:

R$_2$ is a monocyclic or bicyclic aryl or heteroaryl group, which group may be substituted with one or more substituents, selected from the group consisting of halogen, (C$_1$–C$_4$)alkyl, nitro, (C$_1$–C$_4$)haloalkyl, phenyl, phenoxy, (C$_1$–C$_4$)alkoxy and cyano, with the proviso that the alkoxy substituent is not situated in the para position; or wherein R$_2$ is an alkenyl or alkynyl group, which group may be substituted with an optionally substituted monocyclic or bicyclic aryl or heteroaryl group, wherein the substituents are selected from the above-defined group, or with a straight or branched $(C_1-C_8)$alkyl group or $(C_2-C_8)$alkenyl group, which alk(en)yl group may be substituted with one or more substituents selected from the group consisting of halogen, $(C_1-C_4)$alkoxy, $(C_1-C_4)$haloalkoxy, $(C_1-C_4)$alkylthio, $(C_1-C_4)$haloalkylthio, cyano, nitro, phenyl, phenoxy, $(C_3-C_6)$cycloalkyl, and substituted phenyl and phenoxy, wherein the substituents are selected from halogen, $(C_1-C_4)$alkyl, $(C_1-C_4)$haloalkyl, $(C_1-C_4)$alkoxy, $(C_1-C_2)$alkylenedioxy, nitro, cyano, phenoxy and phenyl;

is converted with a carboxylic acid of the general formula

(II)

wherein:

$R_1$ is a straight or branched, saturated or unsaturated, acyclic or cyclic $(C_1-C_{12})$hydrocarbyl group, which group may be substituted with one or more substituents selected from the group consisting of halogen, $(C_1-C_4)$alkoxy, phenyl and substituted phenyl, wherein the substituents are selected from $(C_1-C_4)$alkyl, $(C_1-C_4)$alkoxy, halogen, nitro, $(C_1-C_4)$haloalkyl, and cyano; or wherein $R_1$ is a monocyclic or bicyclic aryl or heteroaryl group, which group may be substituted with one or more substituents selected from $(C_1-C_4)$alkyl, $(C_1-C_4)$alkoxy, halogen, nitro, $(C_1-C_4)$haloalkyl, and cyano;

in the presence of a di$(C_1-C_4)$alkyl azodicarboxylate and a triarylphosphine, to produce an optically active cyanohydrin carboxylic acid ester of opposite configuration, having the general formula

(III)

wherein the symbols have the above meanings.

In using the above method of the invention, the desired optically active cyanohydrin carboxylic acid esters of opposite configuration can be obtained in high yields and enantiomeric purities: e.e. (enantiomeric excess) values of over 90% can easily be reached.

Examples of suitable monocyclic or bicyclic (hetero)aryl groups for substituent $R_2$ are phenyl, naphthyl, pyridyl, furyl and quinolyl. For substituent $R_1$ the following monocyclic or bicyclic (hetero)aryl groups may be considered: phenyl, naphthyl, furyl, pyridyl, quinolyl, thienyl and pyrrolyl. The (hetero)aryl group may be substituted with preferably 1 to 3 substituents, or, in the case of halogen substituents, with up to 5 halogen substituents.

Diethyl azodicarboxylate and triphenylphosphine are preferably used for performing the Mitsunobu esterification of the present invention. Anhydrous aprotic solvents, e.g. ethers such as tetrahydrofuran, are suitable for the esterification reaction under the usual Mitsunobu conditions (see e.g. the above review by Mitsunobu).

The method of the present invention is more in particular intended to convert the optically active cyanohydrins, which are well accessible by using the enzyme mandelonitrile lyase, into the optically active cyanohydrin carboxylic acid esters of opposite configuration. As a consequence, the method of the invention is a convenient tool for synthetizing not easily accessible cyanohydrin carboxylic acid ester enantiomers, which have favourable prospects in crop protection, in particular as insecticides, or for use in liquid crystals, or which possess promising possibilities as synthons for the production of other biologically active substances.

The method of the invention relates more in particular to the conversion of an optically active cyanohydrin of the general formula

(IV)

wherein:

$R_2'$ is a phenyl group, which group may be substituted with 1–3 substituents selected from the group consisting of halogen, $(C_1-C_4)$alkyl, nitro, $(C_1-C_4)$haloalkyl, phenyl, phenoxy and cyano; or wherein $R_2'$ is a pyridyl group; or wherein $R_2'$ is a vinyl group, which group may be substituted with $(C_1-C_4)$alkyl, phenyl or substituted phenyl, wherein the substituents are selected from the above-defined group;

with a carboxylic acid of the general formula II, shown hereinbefore, wherein $R_1$ has the meaning given above 1, under the above-defined Mitsunobu conditions.

Suitable examples of optically active cyanohydrins which can be used as substrates in the Mitsunobu esterification reaction of the invention are the enantiomers of the cyanohydrins of benzaldehyde and of the various position isomers of chlorobenzaldehyde, fluorobenzaldehyde, tolualdehyde, dichlorobenzaldehyde, difluorobenzaldehyde, dimethylbenzaldehyde, trifluoromethyl-benzaldehyde, nitrobenzaldehyde, phenoxybenzaldehyde and cyanobenzaldehyde. Equally useful are the enantiomers of the cyanohydrins of crotonaldehyde and cinnamaldehyde.

Various optically active cyanohydrin carboxylic acid ester enantiomers, obtainable by a Mitsunobu esterification from optically active cyanohydrins having the opposite configuration, are new. Therefore the present invention also relates to an optically active cyanohydrin carboxylic acid ester of a substantial enantiomeric purity, having the general formula

(VIII)

having the S configuration, and
wherein $R_2$ has the meaning given hereinbefore, and $R_1'$ is an optionally substituted phenyl or benzyl group, wherein the substituents are selected from the group consisting of methyl, methoxy, chloro, fluoro, trifluoromethyl, cyano and nitro;

with the proviso, that $R_1'$ is not unsubstituted benzyl if $R_2$ is 2-furyl. Preferably in the above formula VIII compound, $R_1'$ is a phenyl or benzyl group, substituted with one of the above-defined substituents, situated in the para-position.

In a publication by Waldmann (Tetrahedron Lett. 30, 1989, 3057–3058) (S)-α-(phenylacetoxy)(2-furan)acetonitrile is described.

It has been found, that these new cyanohydrin carboxylic acid ester enantiomers generally have favourable physical properties, which allow a relatively easy and simple purification, e.g. by recrystallization, leading to products with a high enantiomeric excess, viz. of at least 95%.

Pre-eminently suitable examples of the above-defined new optically active cyanohydrin carboxylic acid esters according to the invention are the following crystalline compounds:

- (S)-α-(4-nitrophenylacetoxy)benzeneacetonitrile, having a melting point of 89°–90° C.,
- (S)-2-(4-nitrophenylacetoxy)pentenenitrile, having a melting point of 71° C.,
- (S)-α-(4-nitrobenzoyloxy)benzeneacetonitrile, and
- (S)-2-(4-nitrobenzoyloxy)pentenenitrile.

It may be favourable, moreover, to be able to convert the product of the Mitsunobu esterification, i.e. the optically active cyanohydrin carboxylic acid ester of opposite configuration, into the free or unprotected cyanohydrin, of course under conservation of the configuration. Such "free" cyanohydrins are also considered as versatile synthons, e.g. for the production of biologically active substances, or may be converted into more stable intermediates for the synthesis of useful products. For example, the ester function is often not compatible with various desirable subsequent transformations of the cyanohydrin, such as reductions with LiAlH$_4$ or DIBAL and Grignard reactions. Basic hydrolysis of the ester function is not a viable option in this case because of the base lability of the resulting cyanohydrin. Therefore, only solvolysis under acidic conditions may be considered. Under such conditions, however, the cyano group is sensitive to solvolysis. As a special feature of the present invention it has now been found, that under suitable acidic conditions cyanohydrin carboxylic acid esters derived from (cyclo)aliphatic and araliphatic carboxylic acids allow solvolysis without substantial racemization. So by using these preferred carboxylic acids in the Mitsunobu esterification of optically active cyanohydrins, conservation of the configuration in the subsequent solvolysis reaction is ensured, so that as a net result the starting cyanohydrin can conveniently be converted via a Mitsunobu esterification plus subsequent solvolysis into the desired cyanohydrin antipode.

In view of the above, in the Mitsunobu esterification of cyanohydrins according to the invention are preferred carboxylic acids of the general formula

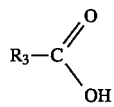  (V)

wherein R$_3$ is a straight or branched, saturated or unsaturated, acyclic or cyclic (C$_1$–C$_{12}$)hydrocarbyl group, which group may be substituted with one or more substituents selected from the group consisting of halogen, (C$_1$–C$_4$)alkoxy, phenyl and substituted phenyl, wherein the substituents are selected from (C$_1$–C$_4$)alkyl, (C$_1$–C$_4$)alkoxy, halogen, nitro, (C$_1$–C$_4$)haloalkyl and cyano.

More in particular, such preferred carboxylic acids can be represented by the general formula

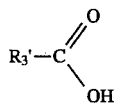  (VI)

wherein:

R$_3$' is a straight or branched (C$_1$–C$_6$)alkyl group, a cyclohexylgroup, or a methyl group substituted with (C$_1$–C$_4$)alkoxy, phenyl, diphenyl or substituted phenyl, wherein the substituents are selected from the group consisting of methyl, methoxy, chloro, fluoro, trifluoromethyl, cyano and nitro.

Alternatively, however, it may be of advantage to obtain by the Mitsunobu reaction a cyanohydrin carboxylic ester, which is suitable for various subsequent transformations and which ester function can therefore be considered as a sufficiently stable protecting group for the cyanohydrin moiety. In view of these considerations it may be desirable to use in the Mitsunobu esterification according to the invention a carboxylic acid of the general formula

  (VII)

wherein:

R$_4$, R$_5$ and R$_6$ are each independently (C$_1$–C$_4$)alkyl, phenyl or phenyl substituted with one or more substituents selected from methyl, methoxy, nitro, halogen and cyano; or wherein R$_4$ is methyl, and R$_5$ plus R$_6$, together with the C-atom to which they are attached, constitute a cyclohexyl group; or wherein R$_4$, R$_5$ plus R$_6$, together with the C-atom to which they are attached, constitute an adamantyl or bicyclooctyl group.

The present invention finally relates to a method of preparing an optically active cyanohydrin from an optically active cyanohydrin antipode, comprising in addition to the Mitsunobu esterification, using the above-defined (cyclo)aliphatic or araliphatic carboxylic acids, the reaction step of acidic solvolysis of the carboxylic acid ester obtained, under conservation of the configuration.

It has been found, that said solvolysis under acidic conditions can best be carried out under the influence of a sulfonic acid, such as methanesulfonic acid, p-toluenesulfonic acid or a polymeric sulfonic acid, preferably in a protic organic solvent, such as methanol or ethanol. It has been proven, that under such conditions the solvolysis occurs smoothly, affording the desired product, i.c. the desired "free" cyanohydrin, without racemization and wherein all functional groups have remained unchanged.

The invention will now be described in greater detail with reference to the following specific Examples.

EXAMPLE I

Mitsunobu esterification

Preparation of (S)-α-(4-nitrophenylacetoxy)benzeneacetonitrile (1)

To a solution of 6.7 g (50 mmol) (R)-α-hydroxybenzeneacetonitrile in 75 ml of dry THF, under nitrogen, are added 14.4 g (55 mmol) triphenylphosphine and 13.6 g (75 mmol) 4-nitrophenylacetic acid. The mixture is cooled to −10° C., after which 8.6 ml (55 mmol) of diethyl azodicarboxylate in THF (total volume 25 ml) are added dropwise in 30 min. After another 15 min at −10° C. the mixture is stirred at room temperature for 4 h, diluted with 200 ml of diethylether and washed successively with a saturated sodium bicarbonate solution (50 ml) and with saturated saline solution (50 ml). After drying over magnesium sulphate, the solvent is evaporated in vacuo. The crude product is recrystallized from dichloromethane/hexane (1/1). Yield 75%. Melting point 89°–90° C.

$[\alpha]_D^{20}$: +11.5° (c=1, CHCl$_3$); e.e.=99%.

$^1$H-NMR: δ(ppm) 3.84 (s, 2H, COCH$_2$Ph); 6.43 (s, 1H, PhCHCN); 7.44 (d, J=8.7 Hz, 2H); 7.47 (m, 5H); 8.20 (d, J=8.7 Hz, 2H).

$^{13}$C-NMR: δ(ppm) 168.31 (CO); 147.14 (arom); 139.61 (arom); 131.05 (arom); 130.44 (arom); 130.20 (arom); 129.12 (arom); 127.69 (arom); 123.63 (arom); 115.63 (CN); 63.45 (CHCN); 39.86 (COCH$_2$).

IR: 3035, 2920, 2240, 1750, 1600, 1510, 1340, 1140, 750, 715 cm$^{-1}$.

In a corresponding manner (S)-2-(4-nitrophenylacetoxy)-pentenenitrile (2) is prepared. The product is recrystallized from dichloromethane/hexane (1/1). Yield 70%. Melting point 71° C.

$[α]^{20}_D$: +15.5° (c=1, CHCl$_3$); e.e. 98%.

$^1$H-NMR: δ(ppm) 1.81 (d, 3H, CH$_3$CH); 3.82 (s, 2H, COCH$_2$Ph); 5.58 (m, 1H, CH$_3$CHCH); 5.81 (d, 1H, CHCN); 6.16 (m, 1H, CHCH$_3$); 7.46 (d, J=8.7 Hz, 2H); 8.22 (d, J=8.7 Hz, 2H).

$^{13}$C-NMR: δ(ppm) 168.25 (CO); 146.86 (arom); 139.84 (arom); 135.84 (CHCHCN); 130.12 (arom); 123.34 (arom); 120.54 (CHCH$_3$); 115.19 (CN); 61.82 (CHCN); 39.63 (COCH$_2$); 17.26 (CH$_3$).

IR: 3060, 2940, 2240, 1745, 1600, 1510, 1350, 1210, 1140, 970, 720 cm$^{-1}$.

In a corresponding manner the following compounds are prepared: nr. compound (3) (S)-α-acetoxy-benzeneacetonitrile
(4) (S)-α-benzoyloxy-benzeneacetonitrile
(5) (S)-α-(4-methoxybenzoyloxy)benzeneacetonitrile
(6) (S)-α-(4-nitrobenzoyloxy)benzeneacetonitrile
(7) (S)-α-methoxyacetoxy-benzeneacetonitrile
(8) (S)-α-phenylacetoxy-benzeneacetonitrile
(9) (S)-α-diphenylacetoxy-benzeneacetonitrile
(10) (S)-α-(4-methoxyphenylacetoxy)benzeneacetonitrile
(11) (S)-2-(4-nitrobenzoyloxy)pentenenitrile The yield (after purification), the enantiomeric excess and the specific rotation are as follows:

| compd. nr. | yield (%) | e.e. (%) | $[α]_D^{20}$ |
| --- | --- | --- | --- |
| (3) | 65 | 92 | −5.8 |
| (4) | 90 | 92 | −24.3 |
| (5) | 85 | 92 | −37.0 |
| (6) | 76 | 99 | −38.6 |
| (7) | 95 | 92 | +7.3 |
| (8) | 95 | 92 | +10.8 |
| (9) | 90 | 92 | +5.1 |
| (10) | 70 | 91 | +2.9 |
| (11) | 75 | 98 | +10.6 |

As compared with the above experiments, some saturated aliphatic cyanohydrins are converted in a corresponding manner as described above:

The product obtained by a Mitsunobu esterification of (R)-2-hydroxy-pentanenitrile with phenylacetic acid is purified by flash column chromatography using EtOAc/hexane (1/9) as the eluent. The product is obtained as a colourless oil. Yield 60%.

The product is identified by $^1$H-NMR, $^{13}$C-NMR and IR spectroscopy. Its physical data reveal, that the R-configuration is retained; the product is identified as (R)-(phenylacetoxy)pentanenitrile.

$[α]_D^{20}$: +61.2° (c=1, CHCl$_3$), e.e. 85%; boiling point 137° C./1.5 mm Hg. The product is identical with the product of the esterification of (R)-2-hydroxy-pentanenitrile with phenylacetic anhydride in dry pyridine.

The above-described Mitsunobu esterification of (R)-2-hydroxypentanenitrile with 4-nitrophenylacetic acid affords (R)-(4-nitrophenylacetoxy)pentanenitrile, so also under retention of the configuration. Yield after purification 70%; e.e. 85%; $[α]^{20}_D$: +51.6°.

EXAMPLE II

Solvolysis

Solvolysis of (S)-α-(4-nitrophenylacetoxy)benzeneacetonitrile (1)

7.35 g (25 mmol) of the above compound (1) are dissolved in a mixture of 40 ml methanol and 100 ml dichloromethane; 25 mmol methanesulfonic acid are added. The reaction mixture is stirred for two days at ambient temperature, after which a solvolysis of 90% (NMR) is observed. Water is added and the product is extracted with dichloromethane (2×50 ml). The combined organic layers are washed with saline solution (2×25 ml), dried over magnesium sulfate, and evaporated in vacuo.

The crude product is silylated with tert.-butyldimethylsilyl chloride TBSCl as follows:

A solution of 3.5 g (50 mmol) imidazole in 75 ml of anhydrous DMF is cooled to 0° C. and 4.5 g (30 mmol) TBSCl are added. After stirring for 15 min said crude above product of the solvolysis (25 mmol) is added, and the resulting mixture is stirred for 1 h at room temperature, poured into 150 ml of water, and extracted with diethyl ether. Work-up gives a yellow oil which is stirred with hexane containing silica gel for 1 h; then the solid is filtered off and washed with cold hexane.

Concentration of the organic layer affords a colourless oil. Yield 70%. $[α]^{20}_D$: −17.5° (c=1, CHCl$_3$); e.e. 96.5% (HPLC).

$^1$H-NMR: δ(ppm) 0.02 (s, 3H, CH$_3$Si); 0.10 (s, 3H, CH$_3$Si); 0.84 (s, 9H, tBu); 5.38 (s, 1H, CHCN); 7.28 (m, 5H, aromatic).

$^{13}$C-NMR: δ(ppm) 136.31 (arom); 128.98 (arom); 128.66 (arom); 125.85 (arom); 119.02 (CN); 63.74 (COTBS); 22.32 ((CH$_3$)$_3$); 17.90 (SiC); −5.34 ((CH$_3$)$_2$Si).

IR: 2920, 1670, 1460, 1260, 1195, 1100, 940, 840 cm$^{-1}$.

The silylated corresponding (R)-enantiomer is known in literature (Brussee et al., Tetrahedron 1990, 46, 979–986). This enantiomer has an $[α]^{20}_D$ of +17° (c=1, CHCl$_3$). The above data indicate that the silyl ether produced is (S)-α-[(tert.-butyldimethylsilyl)oxy]benzene-acetonitrile, and that consequently the product of the solvolysis before silylation is (S)-α-hydroxybenzeneacetonitrile.

In a corresponding manner (S)-2-(4-nitrophenylacetoxy)pentenenitrile (2) is solvolyzed to (S)-2-hydroxypentenenitrile, which is silylated in the same manner as described above with tert.-butyldiphenylsilyl chloride (TBDPSCl). The resulting oil is purified by flash chromatography using dichloromethane/hexane (1/1) as the eluent. Yield 75%.

$[α]^{20}_D$: +4.1° (c=1, CHCl$_3$), e.e. 96.5%.

$^1$H-NMR: δ(PPM) 1.09 (s, 9H, tBu); 1.68 (d, 3H, CH$_3$CH); 4.75 (d, 1H, CHCN); 5.54 (m, 1H, CHCH(O)CN); 5.70 (m, 1H, CH$_3$CH); 7.41 (m, 6H, arom); 7.68 (m, 4H, arom).

$^{13}$C-NMR: δ(ppm) 135.60 (C-4); 131.90 (SiC-arom); 131.52 (SiC-arom); 131.32 (CHCOTBDPS); 130.23 (arom); 130.14 (arom); 127.81 (arom); 127.72 (arom); 125.79 (CH$_3$CH); 118.41 (CN); 63.28 (COTBDPS); 26.51 ((CH$_3$)$_3$); 19.13 (SIC); 17.29 (CH$_3$CH).

IR: 3060, 3040, 2930, 2850, 1660, 1590, 1425, 1100, 1050, 960, 820, 740, 700 cm$^{-1}$.

The silylated corresponding (R)-enantiomer shows an $[α]^{20}_D$ of −4.2°. The above data indicate that the silyl ether produced is (S)-2-[(tert.-butyldiphenylsilyl)oxy] pentenenitrile, and that consequently the product of the solvolysis has also the S-configuration.

We claim:

1. A method of preparing an optically active cyanohydrin derivative from an optically active organohydrin of opposite configuration, comprising the steps of converting an optically active cyanohydrin of the general formula

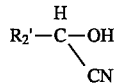
(IV)

wherein:

$R_2'$ is a phenyl group, which group may be substituted with 1–3 substituents selected from the group consisting of halogen, ($C_1$–$C_4$)alkyl, nitro, ($C_1$–$C_4$)haloalkyl, phenyl, phenoxy and cyano; or wherein $R_2'$ is a pyridyl group; or wherein $R_2'$ is a vinyl group, which group may be substituted with ($C_1$–$C_4$)alkyl, phenyl or substituted phenyl, wherein the substituents are selected from the above-defined group;

by reaction with a carboxylic acid of the general formula

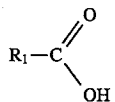
(II)

wherein:

$R_1$ is straight or branched ($C_1$–$C_6$)alkyl group, a cyclohexyl group, or a methyl group substituted with ($C_1$–$C_4$)alkoxy, phenyl, diphenyl or substituted phenyl, wherein the substituents are selected from the group consisting of methyl, methoxy, chloro, fluoro, trifluoromethyl, cyano and nitro; or wherein $R_1$ is an aryl or heteroaryl group, selected from the group consisting of phenyl, naphthyl, furyl, pyridyl, quinolyl, thienyl and pyrrolyl, which group is optionally substituted with 1 to 3 substituents selected from the group consisting of methyl, methoxy, trifluoromethyl, cyano and nitro, or with 1 to 5 halogen substituents; or wherein $R_1$ is a group of the formula

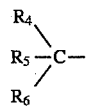

wherein:

$R_4$, $R_5$ and $R_6$ are each independently ($C_1$–$C_4$)alkyl, phenyl or phenyl substituted with one or more substituents selected from methyl, methoxy, nitro, halogen and cyano; or wherein $R_4$ is methyl, and $R_5$ plus $R_6$, together with the C-atom to which they are attached, constitute a cyclohexyl group; or wherein $R_4$, $R_5$ plus $R_6$, together with the C-atom to which they are attached, constitute an adamantyl or bicyclooctyl group in the presence of a di($C_1$–$C_4$)alkyl azodicarboxylate and a triphenylphosphine, to produce an optically active cyanohydrin carboxylic acid ester of opposite configuration in high enantiomeric purity, having the general formula

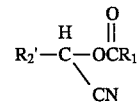
(III)

wherein the symbols have the above meanings.

2. A method as claimed in claim 1, wherein the carboxylic acid has the formula

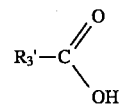
(VI)

wherein:

$R_3'$ is a straight or branched ($C_1$–$C_6$)alkyl group, a cyclohexyl group or a methyl group substituted with ($C_1$–$C_4$)alkoxy, phenyl, diphenyl or substituted phenyl, wherein the substituents are selected from the group consisting of methyl, methoxy, chloro, fluoro, trifluoromethyl, cyano and nitro.

3. A method as claimed in claim 1, wherein the carboxylic acid has the formula

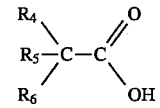
(VII)

wherein:

$R_4$, $R_5$ and $R_6$ are each independently ($C_1$–$C_4$)alkyl, phenyl or phenyl substituted with one or more substituents selected from methyl, methoxy, nitro, halogen and cyano; or wherein $R_4$ is methyl, and $R_5$ plus $R_6$, together with the C-atom to which they are attached, constitute a cyclohexyl group; or wherein $R_4$, $R_5$ plus $R_6$, together with the C-atom to which they are attached, constitute an adamantyl or bicyclooctyl group.

4. A method of preparing an optically active cyanohydrin from an optically active cyanohydrin of opposite configuration, characterized in that a conversion is carried out as claimed in claim 1, producing an optically active cyanohydrin carboxylic ester of the formula

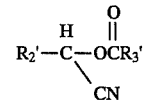
(IX)

wherein $R_2'$ has the meaning given in claim 1, and $R_3'$ has the meaning given in claim 1, after which the compound of the formula IX, thus obtained, is solvolyzed under conservation of the configuration in a protic organic solvent under the influence of a sulfonic acid.

* * * * *